United States Patent [19]

Yamada et al.

[11] Patent Number: 4,656,140
[45] Date of Patent: Apr. 7, 1987

[54] METHOD FOR A MEASUREMENT OF ALCOHOL CONCENTRATION IN ACETIC ACID FERMENTING BROTH

[75] Inventors: Mikio Yamada; Masahiro Mizuno; Yoshinori Tsukamoto; Koki Yamada, all of Handa, Japan

[73] Assignee: Nakano Vinegar Co., Ltd., Handa, Japan

[21] Appl. No.: 669,761

[22] Filed: Nov. 8, 1984

[30] Foreign Application Priority Data

Nov. 18, 1983 [JP] Japan ................. 58-216218

[51] Int. Cl.$^4$ ............... B01D 15/08; C12P 7/54; G01N 1/00; G01N 1/22
[52] U.S. Cl. ............... 436/131; 436/132; 436/175; 436/178; 436/181; 435/140; 435/807; 423/245
[58] Field of Search ............... 436/131, 132, 161, 175, 436/178, 181, 128, 129, 154; 435/807, 291, 140; 423/245 S

[56] References Cited

U.S. PATENT DOCUMENTS

| | | | |
|---|---|---|---|
| 3,252,870 | 5/1966 | Braun et al. | 435/140 X |
| 3,366,456 | 1/1968 | Andreatch et al. | 436/128 X |
| 3,531,373 | 9/1970 | Eder | 435/140 X |
| 3,725,009 | 4/1973 | Lovelock | 436/175 X |
| 4,032,296 | 6/1977 | Hall | 422/89 |
| 4,102,648 | 7/1978 | Hartmann et al. | 436/154 X |
| 4,384,471 | 5/1983 | Wentzel | 436/140 X |

FOREIGN PATENT DOCUMENTS

| | | | |
|---|---|---|---|
| 54-91396 | 7/1979 | Japan. | |
| 1184100 | 3/1970 | United Kingdom | 435/140 |

OTHER PUBLICATIONS

Yamane, Application of Porous Teflon Tubing Method to Automatic Fed-Batch Culture of Microorganisms, Biotechnology and Bioengineering, vol. XXIII (1981), pp. 2509-2524.
Yano, Silicone Tubing Sensor for Detection of Methanol, J. Ferment. Technol., vol. 56, (1978), pp. 421-427.
Merck Index, p. 1228, 10th Edition (1983).

Primary Examiner—Barry S. Richman
Assistant Examiner—Lynn M. Kummert
Attorney, Agent, or Firm—Frishauf, Holtz, Goodman & Woodward

[57] ABSTRACT

A method for measuring the alcohol concentration of an acetic acid fermentation broth which comprises (a) forming a sample gas containing volatile components present in the acetic acid fermentation broth, the volatile components comprising alcohol and acetic acid; (b) passing the sample gas through an absorption column packed with a material which binds acetic acid whereby the acetic acid is absorbed on the material; (c) passing the sample gas which has passed through the absorption column to a gas sensor for measuring the alcohol content of the gas by outputting an electrical signal which correlates to the alcohol content of the sample gas; and (d) determining the alcohol content of the sample gas in response to the electrical output signal from the gas sensor. The invention also provides a method of forming the sample gas by passing a sample of the fermentation broth through a water-repellent gas permeable tube mounted in a hollow cell and passing a carrier gas through the hollow cell whereby volatile components from the fermentation broth inside of the tube diffuse through the gas permeable tube wall and are intermixed with the carrier gas to form the sample gas containing the volatile components.

13 Claims, 3 Drawing Figures

METHOD FOR A MEASUREMENT OF ALCOHOL CONCENTRATION IN ACETIC ACID FERMENTING BROTH

BACKGROUND OF THE INVENTION

This invention relates to a method for measuring the alcohol concentration of an acetic acid fermenting broth.

Generally, the biological activity of acetic acid bacteria is not always constant in a submerged acetic acid fermentation. Therefore, if an alcohol solution as a substrate is added to large excess, a decrease of utilization efficiency of the raw material or a decrease in productivity results due to the high alcohol accumulation in the fermenting broth. On the other hand, if insufficient alcohol is added, the same decrease of productivity occurs due to the deficiency of alcohol in the fermenting broth. In addition to this, if in surface acetic acid fermentation, alcohol which is a substrate, is not still present at the point of discharge, the acetic acid is peroxidized by acetic acid bacteria and it changes the quality of the vinegar greatly for the worse.

As noted hereinbefore, in acetic acid fermentation, the concentration of the alcohol, which is a substrate, is an important factor which significantly influences fermentation conditions. Accordingly, a change of the alcohol feed rate or a determination of discharge is based upon repeated measurement of the alcohol concentration of a fermenting broth taken from the fermentor daily by means of colorimetric determination or gas chromatography in order to maintain good fermentation conditions.

It has been difficult to put these conventional methods for alcohol measurement into practical operation, because it takes too much time until measurement data is obtained after taking a sample from the fermenting broth. In addition, in these methods it has been impossible to determine the concentration from a fermentation stage which varies as the processing proceeds and consequently it impedes good fermentation or results in the production of lower grade or bad vinegar.

A method using a gas sensor such as a Flame Ionization Detector (hereafter FID) or a semiconductor gas sensor has been developed as a method for the measurement of concentration of volatile components in liquid. The principle of this method is based on measuring the concentration of volatile components in gas by introducing a gas attaining equilibrium with the vapor into a gas sensor. In this method, the real concentration of volatile components in a fermenting liquid may be determined by conversion of the concentration of volatile components in the gas to that in liquid.

The following two reports disclose methods using a gas sensor: Ethanol Analysis In Baker's Yeast Fermentation. Biotechnology and Bioengineering, Vol. XXIII, p 2509-2524 (1981); and Methanol Measurement in Biomass Production By Fermentation Using Methanol As A Substrate, J. Ferment. Technol., Vol. 56, No. 4, p 421-427 (1978).

The gas sensor method seems to be very useful for fermentation wherein the volatile component consists of only a single volatile component as mentioned above. However, when a fermenting broth contains plural volatile components which may be detected by the gas sensor, it is substantially impossible to measure only a specific volatile component of the mixture because the gas sensor is not selective.

Fermenting broth in acetic acid fermentation contains two volatile components, alcohol and acetic acid. The FID or semi-conductor gas sensor may detect both and then the electrical signal from the gas sensor may be the output sum of both components. Because of this difficulty when attempting to measure only alcohol which is an important parameter in acetic acid fermentation, it has not been useful to utilize a method that directly analyzes gas concentration using such gas sensors for the measurement of the alcohol concentration of acetic acid fermenting broth. In the following description, without exception, the concentration of alcohol is expressed in volume by volume and the concentration of acetic acid in weight by volume.

It is an object of this invention to provide a method for the measurement of alcohol concentration in acetic acid fermentation.

SUMMARY OF THE INVENTION

The present invention provides a method which can measure accurately and selectively the alcohol concentration from acetic acid fermentation using a gas sensor which detects both alcohol and acetic acid, and has no selectivity for alcohol. We discovered that by introducing the gas from the fermentation containing both gaseous alcohol and acetic acid into an absorption column packed with soda-lime (and preferably heated), the gaseous acetic acid can be entirely absorbed on the soda-lime and only the gaseous alcohol passes through the column without being absorbed on the soda-lime.

The invention is a method for measuring the alcohol (ethanol) concentration of an acetic acid fermenting broth wherein a gas containing volatile components is taken from a fermentor containing an acetic acid fermenting broth. The gas is passed through an absorption column packed with a material which binds acetic acid and the acetic acid content of the gas is absorbed on this material. Then the gas from which acetic acid has been removed is fed to a gas sensor. Alcohol is detected and measured by an electrical output signal from the gas sensor which is read, usually after amplification. This invention provides a method for measuring the alcohol concentration of acetic acid fermentation in which acetic acid bacteria oxidize alcohol to acetic acid. There is no limitation regarding the type of acetic acid fermentation. The invention may be utilized with any type of fermentation such as submerged fermentation, surface fermentation, immobilized cell fermentation and immobilized enzyme fermentation.

DESCRIPTION OF THE PREFERRED EMBODIMENTS

Figure 1:
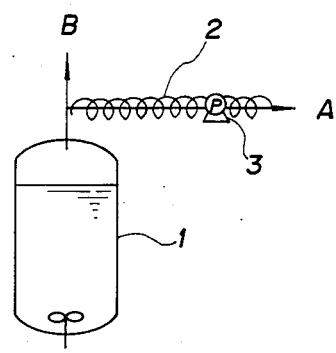
FIGS. 1, 2 and 3 are schematic views showing embodiments of methods for sampling gas containing volatile components.

The absorption of acetic acid gas by an a absorption column packed with a material which binds acetic acid is first described.

EXPERIMENT 1

Three different gases, air containing acetic acid (Gas A), air containing alcohol (Gas B) and air containing both acetic acid and alcohol (Gas C), were prepared. Then, each sample gas was measured according to this invention and according to the conventional technique, and the results were compared. In the method of this invention each of said sample gases was passed through a stainless steel absorption column (diameter 1 cm by length 5 cm) packed with soda-lime and heated to 150° C. The outlet gas from the absorption column was then introduced into a FID (manufactured by SHIMAZU SEISAKUJO CO., LTD.) and the electrical output signal from the FID was measured. In the conventional method, each of said sample gases was directly introduced into the FID. The results are shown in Table 1.

TABLE 1

| Sample gases | | The method of this invention | The conventional method |
|---|---|---|---|
| Gas A | (Acetic acid 200 ppm) | 0 mV | 65 mV |
| Gas B | (Alcohol 500 ppm) | 465 mV | 468 mV |
| Gas C | (Acetic acid 200 ppm - Alcohol 500 ppm) | 463 mV | 531 mV |

The FID output (unit mV) shown in Table 1 is an amplified value. The FID output when only clean air was introduced into the FID was adjusted to zero mV. As is apparent from Table 1, the gas sensor responds to Gas A in the method of the conventional technique, while the gas sensor does not respond to Gas A in the method of this invention. Both methods make the same response to Gas B. From this data, it is found that in the method of this invention only acetic acid gas is absorbed in an absorption column and alcohol gas is not absorbed. With Gas C containing both alcohol and acetic acid, the same output as Gas B is obtained in the method of this invention since the acetic acid in Gas C was absorbed. However, a larger output for Gas C than for Gas B is obtained in the conventional method, which shows that acetic acid is also detected by gas sensor.

The foregoing establishes that it is possible to introduce only alcohol into the gas sensor by first selectively absorbing acetic acid in an absorption column by means of the method of this invention. Although soda-lime was used generally as the material which binds acetic acid, it is possible to similarly use any material which binds acetic acid such as an alkaline solid which neutralizes acetic acid. Such materials include, for example, glass beads on which is coated potassium hydroxide (KOH), sodium hydroxide (NaOH), etc. However, KOH and NaOH are very inconvenient for handling due to their strong deliquescence and furthermore they may dissolve in water if the gas sample for the measurement contains any water and damage the sensor by the absorption of the dissolved alkaline substance on the sensor part. Therefore, it is desirable to use soda-lime which is solid and does not exhibit the aforenoted difficulty when used as a material for absorption of acetic acid.

The following experiment discloses the effect of temperature on an absorption column.

EXPERIMENT 2

(A) water, (B) 2 percent of aqueous alcohol solution and (C) aqueous solution containing 2 percent of alcohol and 5 percent of acetic acid were prepared. 3 Liters of each solution were placed in separate aerobic fermentators and aerated and agitated at 30° C., 800 r.p.m. and 1 liter per minute of air flow rate. The exhaust gases were named Gas A, B and C, respectively. A stainless-steel absorption column (diameter 1 cm by length 5 cm) packed with soda-lime was installed in an oven having a temperature control means for controlling at any desired temperature. After each of said gases was passed through the absorption column, the gas was passed to a FID sensor and the FID output and the time necessary to reach 90 percent response for gas passed through the column at each column temperature were measured as follows: The outlet gas of Gas A was first introduced into the absorption column and then exchanged (replaced) with the outlet gas of Gas B; and the outlet gas of Gas A was first introduced into the absorption column and then exchanged (replaced) with the outlet gas of Gas C. The results were shown in Table 2.

TABLE 2

| Temperature of absorption column (°C.) | Gas exchange A→B | | Gas exchange A→C | |
|---|---|---|---|---|
| | FID output (mV) | Time for 90% (Sec.) | FID output (mV) | Time for 90% (Sec.) |
| 40 | 93.9 | 85 | 103 | 110 |
| 60 | 93.6 | 53 | 98.5 | 58 |
| 80 | 93.9 | 41 | 94.8 | 43 |
| 100 | 94.3 | 35 | 94.4 | 36 |
| 140 | 95.5 | 28 | 95.2 | 30 |
| 180 | 96.4 | 23 | 96.1 | 22 |
| 200 | 97.1 | 20 | 97.1 | 20 |
| 230 | 97.5 | 19 | 97.7 | 19 |
| 250 | 98.2 | 19 | 98.1 | 19 |

The FID output shown in Table 2 means the amplified value. The output when Gas A was introduced was adjusted to zero mV. It is apparent from Table 2, at temperatures higher than 80° C. both Gas C containing acetic acid and Gas B containing no acetic acid showed almost the same FID output. At temperatures lower than 80° C. Gas C showed a larger output than that of Gas B. This means that it is impossible to accurately measure only alcohol because acetic acid was not absorbed sufficient on the soda-lime at these temperatures below about 80° C. Furthermore, the higher the temperature, the shorter the time for reaching the 90 percent response, and the measurement can be performed rapidly. An upper temperature limit for the absorption column should be around 250° C. by considering (i) maintenance, (ii) exchange of the absorption packing for acetic acid, and (iii) the breakdown of equipment at high temperatures. Preferably, the temperature should be from 100° to 200° C. for the advantages of fast response time and maintenance of equipment.

Any type of gas sensor capable of responding to alcohol may be used in principle as a gas sensor in the method of this invention. The FID detector and the semi-conductor gas sensor are advantageous because of long-term stability and reliability. More particularly, the FID sensor may be the most suitable detector for the accurate measurement of alcohol in acetic acid fermenting broth due to its particularly high precision and the linear relationship between alcohol concentration and FID output signal. However, it is necessary to be cautious in handling the FID because of the need to combust hydrogen gas for measurement. In addition the FID detector is high-priced due to the complicated electrical circuit. Contrary to this, the semi-conductor gas sensor is slightly inferior to the FID detector in accuracy and a logarithmic relationship exits between the alcohol concentration and electrical output signal from the sensor. For this reason, the accuracy becomes particularly poor when measuring alcohol concentration higher than 1 percent without pretreatment of sample gas by a method such as dilution before the measurement. However, the semi-conductor gas sensor is low priced and easy to handle, and furthermore alcohol may be detected with a simple electrical circuit compared with the FID. For this reason, it has the advantage of being able to reduce the total cost of the entire system for alcohol measurement used in this invention. As noted, an appropriate gas sensor can be selected when the method of this invention is carried out, as each gas sensor has advantages and disadvantages in accuracy, price and handling.

Sampling methods for gas comprising volatile components such as gaseous alcohol include the following:

The first method directly introduces a portion A of the exhaust gas B from a fermentor 1 in which acetic acid fermentation is being carried out with aeration and agitation into the absorption column 2 at a predetermined flow rate through an air pump and then the gas is passed to the gas sensor 3 (see FIG. 1). This method was demonstrated in Experiment 2. It is easily carried out. When using a FID as the detector, the air pump for gas sampling should be installed before the absorption column. When a semi-conductor gas sensor is used, it can be positioned after the absorption column. When acetic acid fermentation is carried out by surface culture, the contact area between the gas in the upper part of the fermentor and fermenting broth is very small. Therefore, there is not always a linear relationship between the alcohol concentration in the fermenting broth and in the gas phase. Therefore, this sampling method is difficult to apply.

Figure 2:
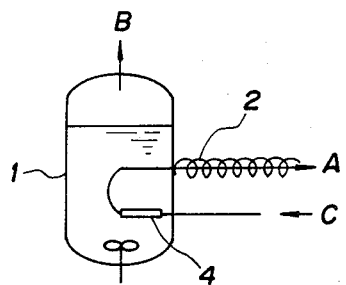

The second method mounts a tube 4 made from a material which is water-repellent and gas permeable inside of the fermentor 1. Both terminals of the tube are connected to an appropriate tubing or pipe such as glass pipe, stainless-steel pipe, etc. Then, a carrier gas C is introduced at a predetermined flow rate into one end of the tube and outlet gas A exits from the other end. This outlet gas A (including carrier gas) is then fed to the absorption column 2 and subsequently to the gas sensor. The carrier gas which is passed through the gas permeable tubing contains those volatile components from the fermenting broth which permeated through the tubing in proportion to the concentration of each of the volatile components in the fermenting broth. Carrier gas containing alcohol and acetic acid is utilized as the sample gas A (see FIG. 2). This second method is generally called the tubing (tube) method and is disclosed in J. Ferment. Technol., Vol. 56, No. 4, p 421–427 (1978) and Published Unexamined Patent Application (Kokai Tokkyo Koho) 54-91396. However, as the acetic acid fermenting broth contains not only alcohol but also acetic acid as the volatile components, both may permeate through the gas permeable tubing and be picked up by the carrier gas. If this carrier gas is directly introduced without any pretreatment into a FID or semi-conductor gas sensor, the gas sensor responds to both alcohol and acetic acid and provides an electrical output signal which is the sum of both components. For this reason, it is necessary to absorb and remove acetic acid by passing the sample gas through an absorption column prior to the introduction into the gas sensor.

These first and second methods are both well-known as sampling methods for gas. Alcohol vapor pressure (mole fraction) in the gas phase also varies as the temperature and pressure inside the fermentor is changed. Thus, the alcohol concentration of a sample gas could vary in response to a change of temperature and pressure, assuming that the alcohol concentration in the fermenting broth is constant. In order to measure the alcohol concentration accurately it is essential to correct against temperature and pressure variations. For example, in acetic acid fermentation by surface culture, temperature control of the fermenting broth is generally not carried out. The temperature of the fermenting broth varies according to the fermentation stage, seasons and so forth. Similarly, in submerged fermentation, although temperature control of the fermenting broth could be performed by passing cooling water through a cooling coil mounted inside of the fermentor, it is very difficult to accurately control temperature to be constant. A variation of about 0.5° C. can always be observed in general.

Figure 3:
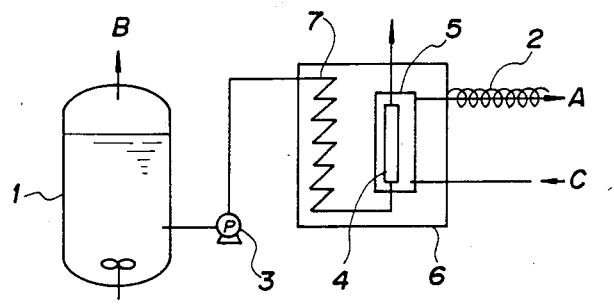

More particularly, in a submerged fed-fermentation, wherein fermentation is continued with the feed of the alcohol solution, the volume of the fermenting broth is increased by feeding the alcohol solution and results in a change of pressure in the fermenting broth in a fermentor. Repeatedly, a correction for variation in temperature and pressure is necessary in order to accurately measure the alcohol concentration in the two methods mentioned above. The inventors have developed a new sampling method to accurately measure the alcohol concentration in acetic acid fermenting broth of which temperature and liquid volume are not constant without the need to correct for temperature and pressure variation. This third method is characterized in that a hollow cell 5 equipped with a water-repellent and gas permeable tube 4 is used in combination with the fermentor 1. Fermenting broth from the fermentor 1 is then introduced continuously into said permeable tube 4 and simultaneously air or nitrogen gas as a carrier gas C is introduced into the portion of the hollow cell 5 surrounding said tube 4. Volatile components in the fermenting broth permeate through the permeable tube as a result of the contact of liquid and gas into the portion of the hollow cell surrounding said permeable tube. These permeated volatile components are carried by the carrier gas into a gas sensor as the sample gas A (see FIG. 3).

In this third method, a portion of the fermenting broth pumped by pump 3 from the fermentor 1 is adjusted to an appropriate temperature, for example 40° C., by passing through a narrow tubing coil 7 for heat-exchange, mounted in a temperature controlled bath 6 of which temperature is, for example controlled to be 40° C. This liquid sample is introduced into the permeable tube 4 mounted in the hollow cell 5 which is positioned in the same temperature controlled bath 6. The fermentation broth passed through the permeable tube 4 is taken from the temperature controlled bath and then exhausted into the atmosphere at a constant height. In this way, the variation of pressure on the fermenting broth in the hollow cell may be minimized to be a very small fraction of atmospheric pressure.

As noted hereinbefore, using the third method it becomes possible to introduce alcohol and acetic acid, which are volatile components from a fermenting broth and permeate them through a permeable tube at constant temperature and pressure, into a carrier gas. Thus, the alcohol content of a fermenting broth may be accurately measured without equipment for correction for temperature and pressure variation.

In this invention, although the sample gas may be obtained by any of said three methods, the third method is the most suitable for an accurate and simple measurement of alcohol concentration. As said sample gases contain water vapor close to the saturation condition in all three methods, the sample gas line should be heated to prevent formation of liquid.

Alcohol detected by the gas sensor is converted into an electrical output and then it is conveniently amplified and read. According to this invention, it becomes possible to rapidly and continuously measure the alcohol concentration of an acetic acid ferementing broth.

The following examples illustrate this invention.

EXAMPLE 1

The alcohol concentration of a fermenting broth from acetic acid fermentation by semi-continuous culture was continuously measured. A glass cell equipped with a gas permeable tube, which is a porous tetrafluoroethylene tube having about 60 percent porosity and inside-diameter, outside-diameter and length of 3.5 mm, 4 mm and 5 cm, respectively, was installed inside of a temperature controlled bath which was connected to a fermentor. Fermenting broth taken from the fermentor through a conduit by a pump is introduced into the permeable tube through a coil for heat-exchange mounted in the above temperature controlled bath and simultaneously fresh air as carrier gas is carried at the flow rate of 40 ml per minute into the above glass cell.

While the carrier gas passes through the permeable tube, the volatile components permeate into the carrier gas. Fermenting broth was introduced continuously into the permeable tube and sample gas was taken out continuously for 40 hours. This sample gas was then diluted twenty times with fresh air and then introduced into an absorption column which is packed with soda-lime containing particles of a size of about 5 mm in a stainless steel pipe (inside-diameter 1 cm by length 5 cm) and mounted in a bath, the temperature of which was controlled to be 180° C. The sample gas which had been passed through the absorption column was fed to an N-type semi-conductor gas sensor (manufactured by FIGARO ENGINEERING INC.) and alcohol was detected and measured by the resultant electrical signal. As this electrical signal has a logarithmic relationship to the alcohol concentration, an appropriate electrical circuit was utilized to linearize the output reading. This electrical signal was amplified with an appropriate amplifier. Prior to the above experiment a calibration curve with the same operation was obtained by passing water and 1 percent or 2 percent standard ethanol solution in place of the fermenting broth. Separately the alcohol concentration in the fermenting broth was measured by measurement from the fermenting broth every 3 to 8 hours by customary gas chromatography and the alcohol content was also measured in accordance with the procedure of this invention. The results are shown in Table 3.

TABLE 3

| Lapse of time (hr) | Alcohol concentration (%) | |
|---|---|---|
| | The method of this invention | The conventional method |
| 0 | 2.53 | 2.51 |
| 3 | 2.36 | 2.36 |
| 6 | 2.03 | 2.08 |
| 10 | 1.99 | 1.97 |
| 15 | 2.24 | 2.25 |
| 18 | 2.45 | 2.43 |
| 21 | 3.01 | 3.04 |
| 24 | 2.58 | 2.58 |
| 27 | 2.02 | 1.99 |
| 31 | 1.45 | 1.45 |

TABLE 3-continued

| Lapse of time (hr) | Alcohol concentration (%) | |
|---|---|---|
| | The method of this invention | The conventional method |
| 34 | 1.00 | 1.00 |
| 40 | 0.50 | 0.52 |

As is apparent from Table 3, it was found that the alcohol concentration measured by the method of this invention was almost the same as that measured by customary gas chromatography and establishes that it is possible to accurately measure the alcohol concentration of an acetic acid fermenting broth. Since it is also possible to measure the alcohol concentration rapidly and continuously, a desirable fermentation control can be carried out. Additionally, savings in time and labor are possible because the sampling method can be automated. Furthermore, the adjustment of the feed rate of the alcohol solution and the discharge of the fermenting broth at an appropriate alcohol concentration may be performed automatically in acetic acid fermentation such as a submerged acetic acid fermentation with inputting the data from the detector for alcohol measurement into a calculation circuit such as a micro-computer and outputting the data calculated after comparison and calculation by a calculation circuit, and it also becomes possible to automate the entire fermentation monitoring and thereby automate control of the fermentation process.

What is claimed is:

1. A method for continuously measuring the ethanol concentration of an acetic acid fermentation broth which contains ethanol and acetic acid as volatile components which comprises
    (a) contacting one side of a water-repellant gas permeable membrane with said fermentation broth so that said volatile components diffuse through to the other side of said gas permeable membrane and carrying said diffused volatile components from said gas permeable membrane as a sample gas;
    (b) passing said sample gas through an absorption column packed with granular soda-lime at a temperature of between 80° C. and 250° C. whereby said acetic acid is absorbed by said soda lime and the remainder of said sample gas containing said ethanol exits from said absorption column;
    (c) passing the sample gas which has passed through said absorption column to a gas sensor for measuring the ethanol content of said gas by outputting an electrical signal which correlates to the ethanol content of said sample gas; and
    (d) determining the ethanol content of said sample gas in response to the electrical output signal from said gas sensor.

2. The method of claim 1 wherein said gas sensor is a Flame Ionization Detector or a semi-conductor sensor.

3. The method of claim 1, wherein said water-repellent gas permeable membrane comprises a hollow tube which is positioned in said fermentation broth so that said volatile components diffuse into the inside of said tube and whereby a carrier gas is passed through said tube to carry said diffused volatile components as the sample gas.

4. The method of claim 3, wherein said temperature is between 80° C. and 200° C.

5. The method of claim 1 wherein said sample gas containing said volatile components is formed by passing a sample of said fermentation broth through a tube having a water-repellent gas permeable tube wall mounted inside of a hollow cell, passing a carrier gas into the portion of said hollow cell surrounding said water-repellent gas permeable tube whereby volatile components from said fermentation broth in said tube diffuse through said gas permeable tube wall and are intermixed with the carrier gas in said hollow cell surrounding said tube thereby forming said sample gas containing said volatile components.

6. The method of claim 12 wherein (i) the sample of said fermentation broth which is passed through said tube and (ii) said hollow cell including said tube, are at substantially the same temperature which is maintained constant.

7. The method of claim 13 wherein said carrier gas is passed into said hollow cell at a position proximate the position wherein said fermentation broth passes into said tube and wherein said sample gas is exited from said hollow cell at a position proximate the position wherein said fermentation broth exits said tube.

8. The method of claim 1 wherein said temperature is between 80° C. and 200° C.

9. The method of claim 8 wherein said sample gas containing said volatile components is formed by passing a sample of said fermentation broth through a tube having a water-repellent gas permeable tube wall mounted inside of a hollow cell, passing a carrier gas into the portion of said hollow cell surrounding said water-repellent gas permeable tube whereby volatile components from said fermentation broth in said tube diffuse through said gas permeable tube wall and are intermixed with the carrier gas in said hollow cell surrounding said tube thereby forming said sample gas containing said volatile components.

10. The method of claim 9 wherein (i) the sample of said fermentation broth which is passed through said tube and (ii) said hollow cell including said tube, are at substantially the same temperature which is maintained constant.

11. The method of claim 10 wherein said carrier gas is passed into said hollow cell at a position proximate the position wherein said fermentation broth passes into said tube and wherein said sample gas is exited from said hollow cell at a position proximate the position wherein said fermentation broth exits said tube.

12. The method of claim 1 wherein the electrical output signal from said gas sensor is amplified and said amplified signal is utilized to determine the ethanol content of said sample gas.

13. The method of claim 12 wherein said gas sensor is a Flame Ionization Detector or a semi-conductor sensor.

* * * * *

UNITED STATES PATENT AND TRADEMARK OFFICE
CERTIFICATE OF CORRECTION

PATENT NO. : 4,656,140

DATED : April 7, 1987

INVENTOR(S) : YAMADA et al

It is certified that error appears in the above-identified patent and that said Letters Patent is hereby corrected as shown below:

Title page, Abstract, line 5, change "componentscomprising"
to --components comprisng--.

Column 9, line 11 (claim 6), change "claim 12"
to --claim 5--.

Column 9, line 16 (claim 7), change "claim 13"
to --claim 6--.

Column 10, line 20 (claim 12), change "claim 1"
to --claim 11--.

Signed and Sealed this

Ninth Day of February, 1993

Attest:

STEPHEN G. KUNIN

*Attesting Officer*  *Acting Commissioner of Patents and Trademarks*